(12) United States Patent
Bruns et al.

(10) Patent No.: US 6,439,966 B2
(45) Date of Patent: Aug. 27, 2002

(54) HAND-HOLDABLE GAS/ABRASION APPARATUS

(75) Inventors: Craig R. Bruns; Mark S. Fernwood; Thomas S. Blake, all of Danville, CA (US)

(73) Assignee: Danville Manufacturing Inc., San Ramon, CA (US)

( * ) Notice: Subject to any disclaimer, the term of this patent is extended or adjusted under 35 U.S.C. 154(b) by 0 days.

(21) Appl. No.: 09/922,379

(22) Filed: Aug. 2, 2001

Related U.S. Application Data
(60) Provisional application No. 60/223,008, filed on Aug. 4, 2000.

(51) Int. Cl.[7] .............................. B24B 1/00; B24C 9/00
(52) U.S. Cl. .......................... 451/38; 451/99; 451/102; 451/90; 451/60; 433/84; 433/88; 433/125
(58) Field of Search ..................... 451/75, 99, 102, 451/101, 90, 36, 38, 40, 60; 433/216, 88, 87, 125, 80, 84

(56) References Cited

U.S. PATENT DOCUMENTS

| | | | |
|---|---|---|---|
| 2,696,049 A | | 12/1954 | Black |
| 4,174,571 A | * | 11/1979 | Gallant ..................... 433/216 |
| 4,648,840 A | | 3/1987 | Conger |
| 4,950,160 A | * | 8/1990 | Karst ........................... 433/88 |
| 5,203,698 A | * | 4/1993 | Blake et al. ................. 433/88 |
| 6,004,191 A | | 12/1999 | Schur |
| 6,287,180 B1 | * | 9/2001 | Hertz ........................... 451/99 |

* cited by examiner

Primary Examiner—Timothy V. Eley
(74) Attorney, Agent, or Firm—Cooley Godward LLP (57) ABSTRACT

A hand-holdable apparatus useful for abrading a surface is provided. The invention is particularly useful for dental applications using a stream of abrasive particles suspended in a gas stream to abrade the surface of a tooth. The apparatus of the invention may be modified to easily minimize "bleed down" of the gas/abrasive stream using a pinch valve and to remove worn flexible conduits for routine maintenance and autoclaving of the apparatus. The apparatus of the invention also provides a novel pick-up assembly for delivery of abrasive particles.

51 Claims, 9 Drawing Sheets

HAND-HOLDABLE GAS/ABRASION APPARATUS

CROSS REFERENCE TO RELATED APPLICATIONS

This application claims the benefit of. U.S. Provisional Application No. 60/223,008, filed on Aug. 4, 2000.

FIELD OF THE INVENTION

This invention relates to a hand-holdable apparatus useful for abrading a surface, particularly the surface of a tooth using a stream of abrasive particles suspended in a gas stream. The invention is particularly useful for dental applications. The apparatus of the invention may be modified to easily minimize "bleed down" of the gas/abrasive stream using a pinch valve and to remove worn flexible conduits for routine maintenance of the apparatus. The apparatus of the invention also provides a novel pick-up assembly for delivery of abrasive particles.

BACKGROUND OF THE INVENTION

A significant technology has developed relating to the use of small abrasive particles propelled by a compressed gas and directed against a surface to clean or abrade the surface. This gas/abrasion technique has developed to a significant degree for dental uses for doing pit and fissure work as well as for cutting enamel and dentin of teeth to repair cavities. In the dental field, the gas/abrasion technique has certain advantages over drilling with a high speed drill, e.g., less heat and pressure are generated. The early gas abrasive devices were cumbersome in that they required an abrasive particle container that was maintained separately from the nozzle means used to direct the stream of gas/abrasive particles against the surface of a tooth. See e.g., U.S. Pat. No. 2,696,049. Over the years devices were developed wherein the abrasive particles were contained in a holder that was associated with a nozzle as a hand-held unit. See for example U.S. Pat. No. 4,648,840. One of the problems with previous devices is that the control of the flow was done using a foot peddle, which did not give the user detailed control of the flow of the gas abrasive stream and often resulted in long bleed down times. We have now invented a hand holdable device having a flexible design allowing the user to regulate flow using a finger control and to minimize the bleed-down time when shutting off the gas/abrasive stream. The design also provides for the use of a pinch valve mechanism on a flexible line to regulate the flow of material. Preferably the flexible line is removable and thus making the hand holdable device autoclavable.

SUMMARY OF THE INVENTION

One aspect of this invention is an apparatus for delivering a stream of a mixture of a gas and a powdered abrasive material to a surface. The apparatus comprises:
(a) a container-receiving member for detachably receiving a container for the powdered abrasive material;
(b) a discharge nozzle for directing the stream of the mixture of the gas/abrasive material against a surface;
(c) a first optionally flexible conduit having one end in fluid communication with the discharge nozzle and the other end in fluid communication with the container, when attached, through the container-receiving member;
(d) a second optionally flexible conduit for connecting one end to an external gas source and the other end to the attachment portion for the abrasive material container;
(e) a pinch valve for pinching either the first or second flexible conduit to regulate the flow of the mixture of the gas/abrasive material to the discharge nozzle; and
(f) a housing for parts (a)–(e).

Another aspect of this invention is a hand-holdable apparatus for delivering a stream of a gas and a powdered abrasive material to a surface. The apparatus comprises:
(a) an abrasive material pick-up assembly comprising (i) a container-receiving member for detachably receiving a container for the powdered abrasive material, (ii) two conduits, an inner conduit defined by a surrounding wall having a distal end away from the container-receiving member and proximal end connected to the container-receiving member and an outer conduit defined by an outer wall, having analogous distal and proximal ends, wherein an intermediate passage is defined by the inner conduit wall and the outer-conduit wall, (iii) a container for holding the powdered abrasive material, the container having an open end and a closed end, which container is detachably connected to the container-receiving member through its open end and encloses the two conduits such that distal ends of the conduits are near the closed end of the container, (iv) a passageway through the wall of the inner conduit near its distal end, and (v) an optional passageway through the wall of the outer conduit near its distal end;
(b) a discharge nozzle for directing a stream of a pressurized gas/abrasive mixture from the container against a surface to abrade the surface;
(c) a gas delivery entry line for delivering a pressurized gas to the interior of the container through one of the conduits;
(d) an exit line communicating with the interior of the container and leading to the discharge nozzle;
(e) a pressure-actuated member that interrupts the flow of the gas/abrasive mixture from the container to the discharge nozzle, wherein when a pressurized gas is directed through the entry line into the inner conduit or intermediate passage, a pressure differential is created to draw the powdered abrasive material from the container out the exit line and to the nozzle.

Another aspect of this invention is a process for abrading a surface by delivering a stream of a mixture of a pressurized gas and a powdered abrasive material to the surface. The process comprises:
(A) connecting a source of pressurized gas to a hand-holdable apparatus that comprises
(a) a container-receiving member detachably attached to a container containing a powdered abrasive material;
(b) a discharge nozzle for directing the stream of the mixture of the gas/abrasive material against the surface;
(c) a first optionally flexible conduit having one end in fluid communication with the discharge nozzle and the other end in fluid communication with the attached container through the container-receiving member;
(d) a second optionally flexible conduit for connecting one end to an external gas source and the other end to the attachment portion for the abrasive material container;
(e) a manually-operated pinch valve for pinching either the first or second flexible conduit to regulate the flow of the mixture of the gas/abrasive material to the discharge nozzle; and
(f) a housing for parts (a)–(e), (B) directing the discharge nozzle against a surface to be abraded, and (C) actuating the pinch valve to allow a stream of pressurized gas/abrasive material to impinge upon the surface for a time sufficient to abrade the surface.

Another aspect of this invention is a process for abrading a surface by delivering a stream of a mixture of a pressurized gas and a powdered abrasive material. The process comprises (A) connecting a source of pressurized gas to a hand-holdable apparatus that comprises
   (a) an abrasive material pick-up assembly comprising (i) a container-receiving member for detachably receiving a container for the powdered abrasive material, (ii) two conduits, an inner conduit defined by a surrounding wall having a distal end away from the container-receiving member and proximal connected to the container-receiving member and an outer conduit defined by an outer wall, having analogous distal and proximal ends, wherein an intermediate passage is defined by the inner conduit wall and the outer-conduit wall, (iii) a container for holding the powdered abrasive material, the container having an open end and a closed end, which container is detachably connected to the container-receiving member through its open end and encloses the two conduits such that distal ends of the conduits are near the closed end of the container, (iv) a passageway through the wall of the inner conduit near its distal end, and (v) an optional passageway through the wall of the outer conduit near its distal end;
   (b) a discharge nozzle for directing a stream of a pressurized gas/abrasive mixture from the container against a surface to abrade the surface;
   (c) a pressurized gas delivery entry line for delivering a pressurized gas to the interior of the container through one of the conduits;
   (d) an exit line communicating with the interior of the container and leading to the discharge nozzle;
   (e) a pressure-actuated member that interrupts the flow of the gas/abrasive mixture from the container to the discharge nozzle, wherein when a pressurized gas is directed through the entry line into the inner conduit or intermediate passage, a pressure differential is created to force the powdered abrasive material from the container out the exit line and to the nozzle.

(B) directing a stream of gas/abrasive material from the discharge nozzle against a surface to be abraded, and (C) allowing the pressurized gas to flow into the container to force the pressurized gas/abrasive material to impinge upon the surface for a time sufficient to abrade the surface.

DETAILED DESCRIPTION AND PRESENTLY PREFERRED EMBODIMENTS

One aspect of this invention is an apparatus for delivering a stream of a mixture of a gas and a powdered abrasive material to a surface. The apparatus is of a size that can easily be held in one hand and has a housing that includes:
   (a) a container-receiving member for detachably receiving a container for holding the powdered abrasive material;
   (b) a discharge nozzle for directing the stream of the mixture of the gas/abrasive material against a surface;
   (c) a first flexible conduit having one end in fluid communication with the discharge nozzle and the other end in fluid communication with the container (when attached) through the container-receiving member;
   (d) a second flexible conduit for connecting one end to an external pressurized gas source and the other end to the attachment portion for the abrasive material container; and
   (e) a pinch valve for pinching either the first or second flexible conduit to regulate the flow of the mixture of the gas/abrasive material to the discharge nozzle.

Figure 1:
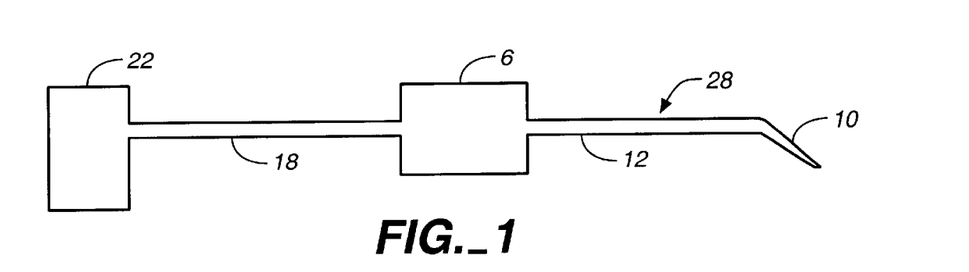
FIG. 1 is a simple schematic diagram of one aspect of this invention where the control valve is between the abrasive container and the exit nozzle.
Figure 2:
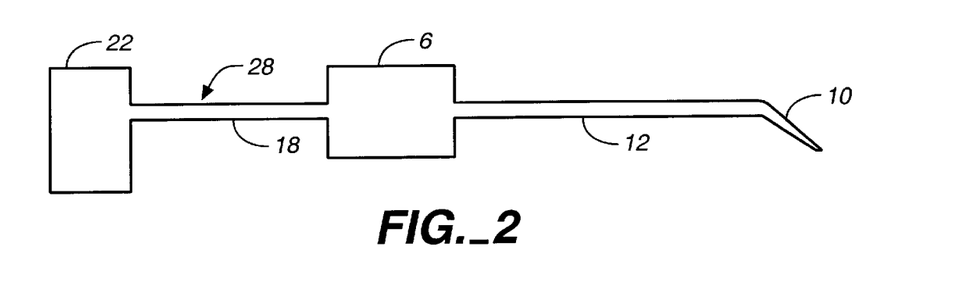
FIG. 2 is a simple schematic diagram of another aspect of this invention where the control valve is between the pressurized gas supply and the abrasive container.

Turning first to FIG. 1, we see a simple schematic diagram of one aspect of the invention where the pinch valve is between the abrasive container and the discharge nozzle. Here the hand-holdable device has a container 6 and a pinch valve 28 located between the container, which holds the abrasive material, and the discharge nozzle 10. A pressurized gas supply 22, which is generally found as pressurized air in dentists' office, is the source of the pressurized gas for mixing with the abrasive material and exiting the nozzle of the discharge nozzle 10. Thus, the pressurized gas enters the container 6, mixes with the powdered abrasive material and exits flexible line 12, where the flow of the pressurized gas and powdered abrasive material is regulated by valve 28. Alternatively, in FIG. 2 the valve 28 is located on a flexible line 18 between the supply of the pressurized air 22 and the container holding abrasive powdered material in container 6. Here, when valve 28 pinches line 18 there is a slightly higher level of bleed down through the discharge nozzle 10 once the valve 28 is closed. While the schematic concept set forth in FIG. 2 is useful that of FIG. 1 is preferred.

Figure 3:
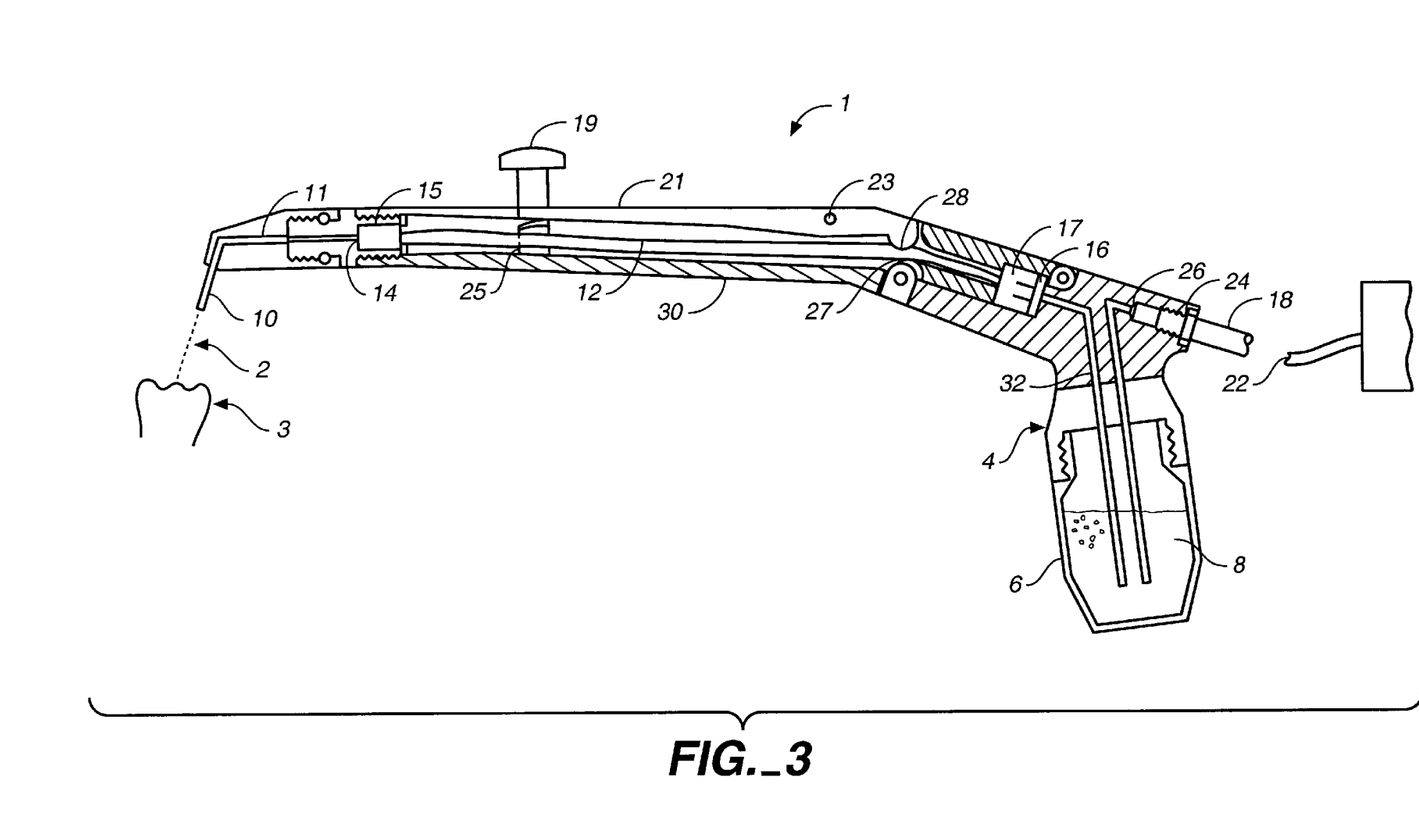
FIG. 3 is a side cut-away view of a first embodiment of the invention.

Turning now to FIG. 3, one sees in greater detail an apparatus 1 for delivering a stream 2 of a mixture of a gas and powdered abrasive material to a surface 3. This detailed figure shows a device of FIG. 1. The stream 2 is directed at the surface for a time sufficient to abrade the surface as desired. Preferably the surface will be that of a tooth, for the apparatus finds its primary use in dental applications. The apparatus comprises several parts. The first is a container receiving member 4 for detachably receiving a container 6 that holds the powdered abrasive material 8. The abrasive material is that used in the air/abrasive dental art and may be of a particle size of less than about 50 microns down to 10 microns or less. Exemplary hard abrasive materials include, by way of example and not limitation, aluminum oxide. Exemplary soft abrasive materials such as for use in cleaning and polishing, include, by way of example and not limitation, sodium bicarbonate and hydrated alumina. While the drawing is shown with the container 6 attached to the container receiving member 4, it is understood that it will be detachably received. Thus the member may be screwed in to form a tight fit so that the container can be pressurized once a pressurized gas is pumped into it. Alternatively the container can be detached using some other mechanism such as set screws or a snap fit cap. In addition, the container can be a disposable single-use design. The container is releasably received into the receiving member 4 so that the container can be pressurized without leakage of the gas.

The apparatus also includes a discharge nozzle 10 for directing the stream 2 of the mixture of the gas/abrasive material against the surface 3. The discharge nozzle can be of any design which is generally known in the art. For example, see U.S. Pat. No. 5,765,759 (for a removable, rotatable nozzle), which is incorporated herein by reference.

The apparatus further includes a first optionally (but preferably) flexible conduit 12 having one end 14 in fluid communication with the discharge nozzle 10 and the other end 16 in fluid communication with the interior of container 6 when it is attached to the container receiving member 4. The first conduit 12 is preferably made of a flexible, material that is generally known in the art. This material may be, for example, a polyurethane, polypropylene, polyethylene, silicone, or other polymeric material that are readily available that can withstand repeated pinching by the pinch valve, if so positioned. A preferred material is a silicon hybrid thermoplastic elastomer called C-FLEX® from Consolidated Polymer Technologies Inc., Largo, Fla. The function of the first conduit 12 is to allow fluid communication between the discharge nozzle 10 and the interior of container 6 to lead the stream of material of pressurized gas and abrasive material to the discharge nozzle and out the apparatus against the surface.

The apparatus will also include a second conduit 18 that is optionally flexible for connecting one end 20 of conduit 18 to an external gas source 22 (which is pressurized) and the other end 24 to the attachment portion 26 for the abrasive material container 6. The function of this conduit is to provide a pathway for the pressurized gas from the external gas source to enter the interior of container 6.

The apparatus further comprises a manually-operated (preferably operated by finger pressure) pinch valve 28 for pinching either the first flexible conduit 12 or the second conduit 18 (when flexible) to regulate the flow of the mixture of gas/abrasive material to the discharge nozzle 10. In FIG. 1, the pinch valve is shown as pinching the first flexible conduit 12 at point 27. While the pinch valve can operate to pinch and therefore regulate the flow of the mixture of gas/abrasive material to the discharge nozzle either at the first or second conduit, the valve located on the first flexible conduit 12 is preferred because that minimizes the amount of abrasive material that will bleed from the end of the discharge nozzle after the pinch valve is actually to stop the flow of pressurized gas. Manually-operated means that the person who is handling the apparatus has control of the valve. The control may be actuated using air pressure, electricity, or finger pressure, preferably the latter.

The housing 30 is designed to have parts (a) through (e) within a unitary arrangement so that the apparatus can be held in the hand of the practitioner. For a dentist, this is particularly useful as they can direct the stream of gas/abrasive material to the surface of the tooth with great precision with the abrasive material contained in the container when attached to the container receiving means. The apparatus is of the size that is easily held in the hand and generally will be between about 6 inches to about 12 inches in length. It will weigh about 4 ounces to no more than a pound. The external gas source is generally available in dentists' offices at a pressure of about 30 to about 140 psi. The housing may be a light metal or plastic, and preferably is an injection molded plastic that is autoclavable. A particularly useful polymer is polyphenylsulfone called RADEL® R 500 available from Amoco Performance Products, Inc., Alpha Retta, Ga. Preferably, the material used for the housing will be characterized by being autoclavable. This characteristic is useful because a dentist can remove the conduit, sterilize the housing by autoclaving and reuse the housing. Alternatively, if the conduit (for example conduit 12) material is autoclavable, the housing, with the conduit in place, can be autoclaved.

A preferred aspect of the invention is the removability of the first flexible conduit 12 when the pinch valve 28 is located to pinch line 12 to regulate the flow of the gas/abrasive material. It is preferred to be removable because the pinch valve squeezing the conduit results in wear at the point of contact. The conduit can easily be removed when it wears. Thus, designing the housing and the positioning of the first conduit aids in the removability of the first flexible conduit 12. In this situation, each end 14, 16 of the flexible conduit 12 is designed so that it is removably connected for easy disengagement. Thus, in FIG. 3, one can see that end 14 has a collar 15 and end 16 has a collar 17, each of which is snugly and releasably retained within the housing to align one end of the flexible conduit with the discharge nozzle 10 and the other end of the flexible conduit with a line 32 communicating with the container 6 for the part of the abrasive material 8 when the container is attached to the container receiving 4.

Because the conduit 12 will be pressurized, the material used is characterized by having an appropriate combination of durometer rating and wall thickness. Generally, the pressure of the system will vary from about 30 pounds per square inch (psi) to about 140 psi. This range allows a dentist to use a lower pressure, e.g., about 30 psi, to do pit and fissure work and a higher pressure, e.g., about 140 psi for cutting enamel and dentin. The durometer rating of the flexible material and for conduit 12 (or other flexible conduits) may vary from a Shore A hardness rating of about 40 to about 90. The lower rating provides a more flexible conduit while the higher rating provides a firmer conduit. The wall thickness is an additional consideration for the material used for the conduit. Generally, for a system having a higher pressure rating, the wall thickness of the conduit will be greater than for a lower pressure rating. One of ordinary skill will recognize the need for balancing the thickness of the wall with the durometer rating to such a balance to handle the pressure without bursting, but still being pinchable by the pinch valve mechanism. Generally, a silicone hybrid tubing having a durometer rating of 70, an inner diameter of about 0.039–0.063 inch, and an outside diameter of about 0.110 to 0.135 inch is particularly useful. An inside diameter of about 0.046 inch and outside diameter of 0.125 is preferred.

As mentioned, the pinch valve may also be located to constrict the second flexible conduit 18 to regulate the flow of the gas/abrasive mixture. This can be seen in FIG. 6 as discussed hereinafter.

The apparatus of FIG. 3 is operated by means of a finger control button 19. The control button is connected to a lever arm 21. The lever arm engages the pinch lever 28, which pivots on a lever pin 23. The flow of the air/abrasive material to the nozzle is controlled by pinching a line 12 at position 27. A spring 25 holds the arm in the "off" position until the finger button is depressed. In the off position, the spring forces the lever 21 at position 28 against the line 12, compressing it against the housing wall, and thereby inhibiting the flow of air and abrasive material. When the switch is depressed, the lever arm 21 lifts the pinch section 28, allowing the supply air/abrasive material to flow to the nozzle 10 through the supply line 12. While the apparatus of FIG. 3 shows a pinch lever 28 pivoting on a lever pin 23 to pinch line 12 at position 27, one of skill in the art will recognize that other mechanisms may be used such as a reciprocating pinch bar, or a spring, air, or electromechanical triggered device.

A compressed gas supply 22 can be found in most environments in which the abrading apparatus will operate, however where no supply exists a pressurized air, carbon dioxide or nitrogen bottle can be provided. In a dental environment, an operating pressure of 30 to 140 pounds per square inch should be supplied, (i,e. the standard pressure of a dentists air supply) however it can be appreciated that the apparatus will operate at a variety of air pressures. Pressurized air is supplied to the apparatus at an air supply port 22. This port can be designed to accommodate a variety of standard fittings such as snap fit, friction fit, or preferrable screw fit.

In addition to the air abrasion conduit 12, the apparatus may also include a water line (not shown) that parallels the conduit 12 and is operated by the same pinch valve. The line is positioned to provide a source of water to the nozzle in a manner that provides a fine mist or curtain flowing from the nozzle, preferably encircling the air/abrasive stream to minimize the distribution of the abrasive particles.

Figure 4:
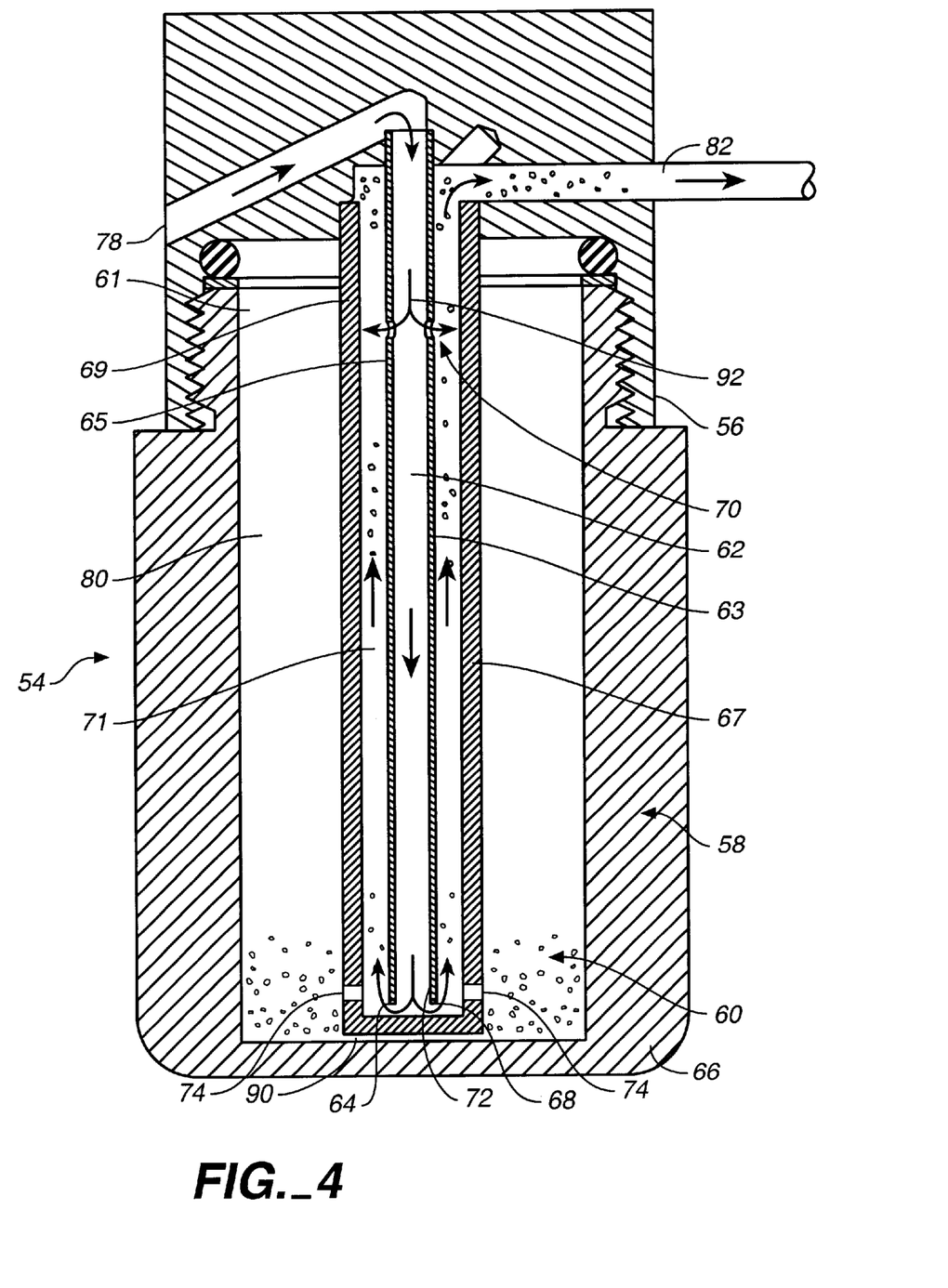
FIG. 4 is a side cut-away view of the abrasive material reservoir assembly.

Turning now to FIG. 4, one sees a preferred abrasive material pick-up assembly, useful with a hand-holdable apparatus for delivering a stream of a gas and powdered abrasive material to a surface. The apparatus comprises a discharge nozzle for directing a stream of pressurized gas/abrasive mixture from the pick-up assembly to the surface, a gas delivery line for delivering the pressurized gas to the interior of the container through one of the conduits, an exit line communicating with the interior of the container leading to the discharge nozzle, and finally a pressure actuated member that interrupts the flow of the abrasive mixture from the container to the discharge nozzle. This is similar in operation to the device of FIG. 1. In more detail, one can see the preferred abrasive material pick-up assembly 54. This assembly comprises several components. The first is a container receiving member 56 for detachably receiving a container 58 for the powdered abrasive material 60. The container 58 acts as a reservoir for the abrasive material 60. The container seats tightly against the container receiving member in a detachable manner by screwing the top of the container into the container receiving member. Alternatively, the container may be frictionally fit into the container receiving member or snugly fit in some other manner to ensure an air tight seal. In order to assure a tight seal of the container against the container receiving member, a rubber gasket not shown is positioned to provide an airtight seal. The pick-up assembly further comprises two conduits, an inner conduit 62, defined by a surrounding wall 63 having a distal end 64 away from the container receiving member 56 and proximal end 65 near the container receiving member 56, and an outer conduit, defined by an outer wall 67 having an analogous distal 68 and proximal 69 ends. An intermediate passage 70 is defined by the inner conduit wall 63 and the outer conduit wall 67. The container 58 for holding the powdered abrasive material 60 has an open end 61 and a closed end 66. The open end of the container is detachably connected to the container receiving means and encloses the two conduits such that the distal ends 64 and 68 of the conduits are near the closed end 66 of the container. Through the distal end 64 of the inner wall 63 of the inner conduit 62 there is a passageway 72. This passageway allows the particles of abrasive material to, depending on which way the air is flowing, enter the inner conduit and be transported out of the container. There is an optional passageway 74 through the wall 67 of the outer conduit 66 near its distal end 68. This optional passageway modifies the rate of flow of the abrasive material out of the container. The apparatus further includes a line 82 (shown as an exit line) for delivering a stream of pressurized gas/abrasive mixture from the container 58 through a discharge nozzle against a surface to abrade the surface. A line 78 (shown as an entry line) is positioned for delivering a pressurized gas into the interior 80 of the container 58 through one of the conduits. An exit line 82 that communicates with the interior 80 of the container 58 leads to discharge nozzle not shown. A pressure actuated valve (not shown) that interrupts the flow of the gas/abrasive mixture out line 82 from the container 58 to the discharge nozzle is present to regulate the flow of the gas/abrasive mixture. When a pressurized gas is directed through the entry line 78 into the inner conduit 62 (or the intermediate passage 70 going the opposite direction) a pressure differential is created to force the powdered abrasive material 60 from the interior of container 58 out the exit line 82 and to the discharge nozzle.

Preferably in this assembly, the exit line leading to the discharge nozzle is flexible, the pressure actuated valve is a pinch valve located between the discharge nozzle and the container receiving member 56 to restrict the flexible exit line 82 to regulate the flow of the gas/abrasive mixture. It is also preferred in this situation to have the flexible exit line removably connected at each end of the line, similar to FIG. 3 each end of the flexible exit line has a collar that is snugly releasably retained to align one end of the flexible exit line with the discharge nozzle and the other end with a line communicating with the container acting as the reservoir for the powdered abrasive material. Alternatively, while not shown in FIG. 4, the gas delivery entry line 78 may also be flexible and the pressure actuated member is a pinch valve located to constrict the gas delivery flexible line to regulate the flow of the gas/abrasive mixture. Again, preferably the gas delivery flexible line is removable with releasable connections at the end of each line. The releasable connections are preferably collars which are snugly and releasably retained to align one end of the flexible line to an external gas source and the other to the container receiving member.

In a preferred embodiment, the conduits of the abrasive material pick-up assembly are positioned to be concentric relative to each other. The outer conduit wall 67 of the abrasive material pick-up assembly has its distal end 68 positioned so that a gap 90 exists between the bottom 66 of container 58 and the distal end 68 of the outer conduit 67. This gap is preferably about 0.035 inch to about 0.125 inch and is preferably about 0.095 inch. The passageway 72 through the distal end 64 wall of the inner conduit 62 has a diameter of about 0.015 to about 0.030 inch, preferably 0.022 inch. It is preferred that there are two passageways through the distal end of the inner conduit 62 wherein each passageway is located approximately 180° from the other. In addition, the inner conduit of the abrasive material pick-up assembly has a passageway 92 through the wall of the inner conduit near its proximal end 65. The passageway 92 near the proximal end of the inner conduit will have a diameter of about 0.025 to about 0.035 inch, preferably about 0.031 inch. While the gas flow into the container 58 will be such that it will force the abrasive particles out through the exit line 82, when the pressurized gas is directed into the inner conduit the gas/abrasive material mixture is directed out of the container 58 through the intermediate passageway 70 formed between the outer wall 63 of the inner conduit 62 and the inner wall 67 of the outer conduit onto the exit line 82 and to discharge nozzle. Alternatively, pressurized gas may be directed into the container 58 through the intermediate passage 70 formed between the outer wall 63 of the inner conduit 62 and the inner wall 67 of the outer conduit 66 and the gas/abrasive material is then directed out of the container 58 through the inner conduit 62.

Figure 5:
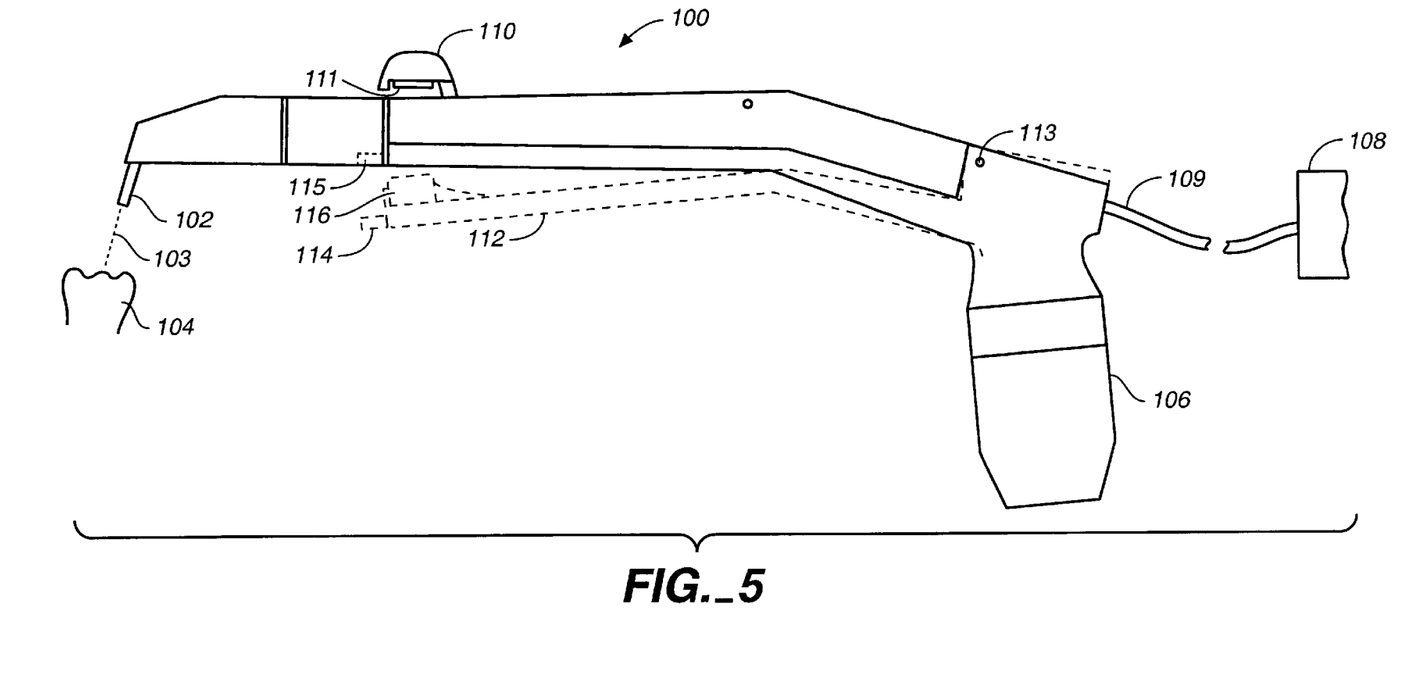
FIG. 5 is a side cut-away view of an apparatus of this invention showing the movement of an arm providing internal access to the apparatus.

Turning now to FIG. 5 one sees a side view of the housing which is designed to hold the various parts of the invention. Here we can see that the housing 100 has a discharge nozzle 102 through which a stream of pressurized gas abrasive particles 103 is directed against the surface 104 of a tooth. The operation of the device is similar to the description for that of FIG. 3 but the internal workings are not shown in this particular figure. One can see that container 106 holds the powdered abrasive material which is used to form the stream with a supply of air. The air supply 108 is connected by supply line 109 to the container which preferably operates in a fashion that is shown in FIG. 4. The finger button 110 corresponds to the button shown as 19 in FIG. 3. Partially exposed at 111 is a spring that will maintain the pinch valve against the flexible line (not shown) to keep the line closed. Upon pressing down on the button the valve will open and operate in accordance with discussion of the device in FIG. 3. As mentioned in the discussion of FIG. 3 the flexible tubing 12 having collars 15 and 17 on either end of the line is preferably removed. Here in FIG. 5 one sees that an arm 112 can pivot downward and allow the flexible line (not shown) to be removed. Shown in dotted line is the collar 116 that was discussed as 15 in the discussion of FIG. 3. The arm swings at pivot point 113 to drop down and provide access to the internal workings of the housing 100. At the end of arm 112 is an extension 114 which snap fits into the receptor 115 and positions the collar as desired internally.

Figure 6:
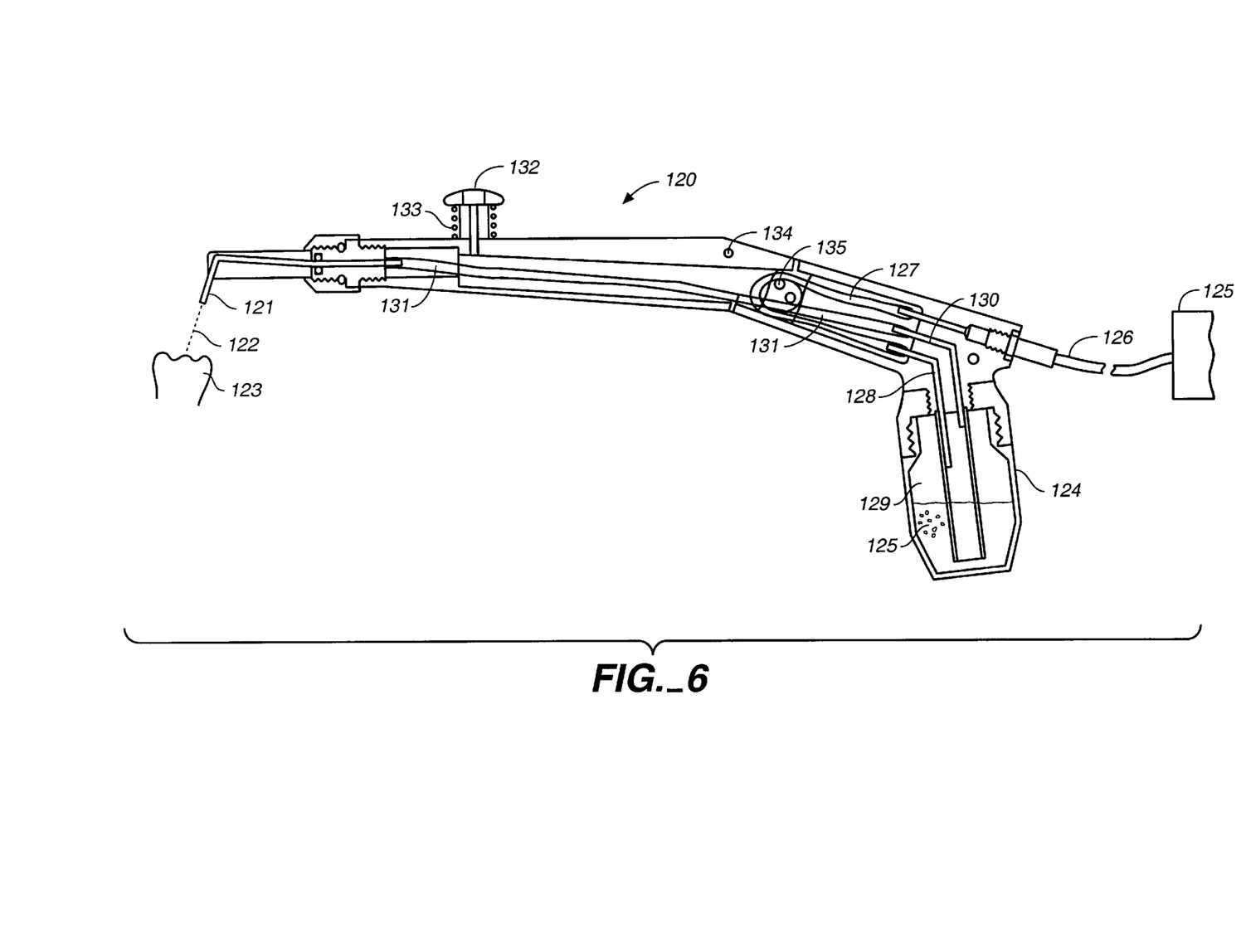
FIG. 6 is a side cut-away view of an apparatus of the invention having a configuration that operates in accordance with FIG. 2.

Turning now to FIG. 6 one sees a cut away view of an aspect of this invention which is consistent with the concept broadly set forth in FIG. 2 where the control valve 28 is located between the pressurized gas supply source 22 and the abrasive containing jar 6. In FIG. 6 different numerals will be used than previously. A housing broadly identified as 120 has a discharge nozzle 121 which emits a stream of gas abrasive particles 122 on to surface 123 to abrade the surface, e.g. a tooth. The powdered abrasive material 125 is contained in container 124 in a manner similar to that described in FIG. 3. The particular design of the container in the pickup assembly may be any type of pickup assembly known in the art but preferably is of the variety shown in FIG. 4. In operation the housing and assembly is connected to air supply source 125 through supply line 126. This is connected internally to a flexible line 127 which leads to an entry tube 128 into container 124 through the interior 129 of container 124. The pressurized gas forms a cloud of the abrasive material 125 and is forced out exit tube 130 into flexible line 131 which leads to the discharge nozzle 121. To control the flow of the material a finger control 132 is used. A spring 133 keeps the finger control in the up position and on the tube 127 at point 135 to squeeze the tube and prevent the gas from flowing to the container 124. When the finger control 132 is pushed down against spring 133 it pivots at pivot point 134 and the pressure against the tube 127 at 135 is released allowing the gas to flow through line 128 into the interior of container 124 and out the exit tube 130 into the flexible tube 131 and to the discharge nozzle 121.

Figure 7:
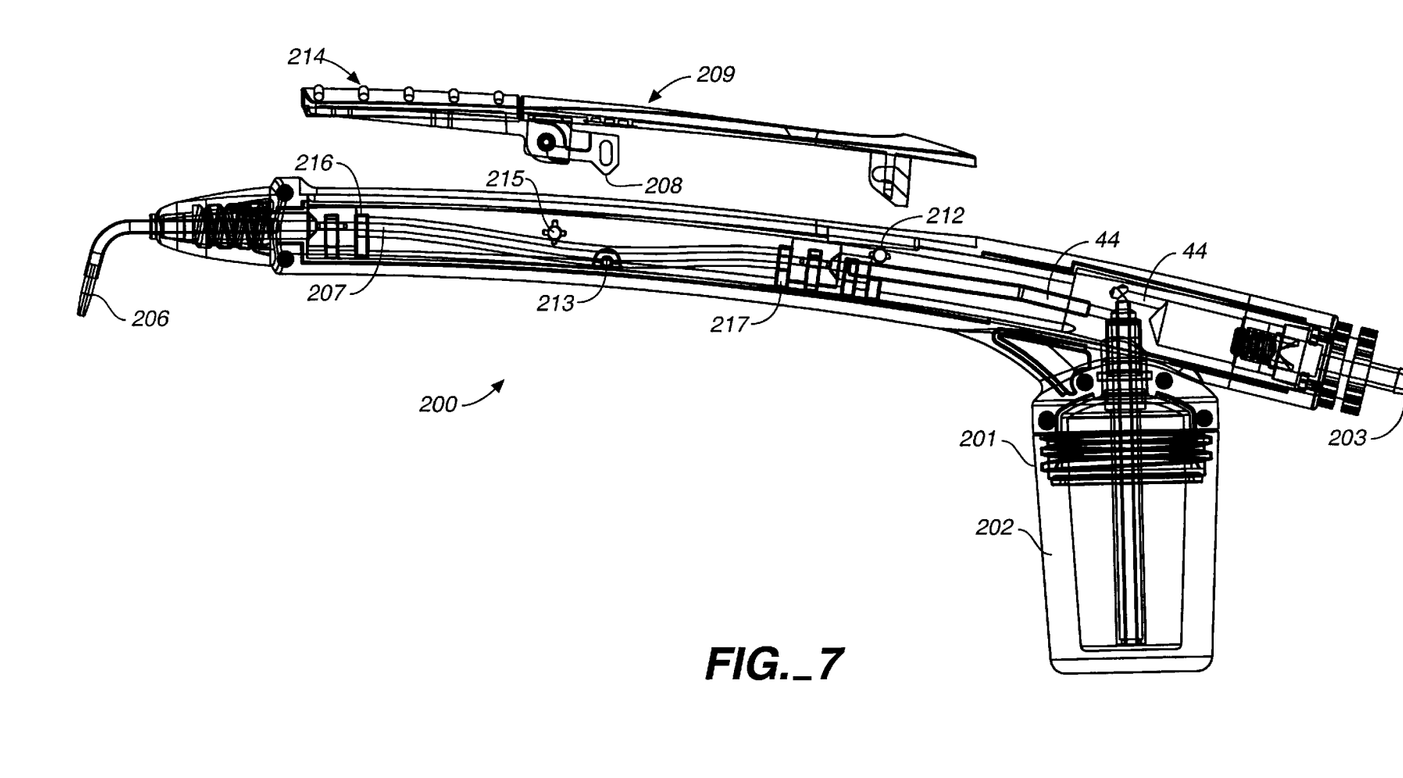
FIG. 7 is a side, exploded, cut-away view of the apparatus of the invention.

FIG. 7 provides a side, exploded view of the apparatus of the invention generally designated as 200. The apparatus has a container-receiving member 201 for receiving container 202, which holds the abrasive particles not shown. In operation the apparatus operates similarly to that explained in the description of FIG. 3. Thus, nipple 203 connects to a pressurized gas source, not shown, through an appropriate tube. The pressurized gas enters container 202 through line 204 and operates as discussed in detail in the section describing FIG. 4. The gas abrasive stream exits container 202 via line 205 and out nozzle 206. The flow is regulated in line 207 by the digitally operated pinch valve having a contact region at 208. The exploded view of FIG. 7 shows a lever 209 that allows access to the interior of apparatus 200 to remove line 207 from the interior before autoclaving and sterilization of the housing. Lever 209 fits into apparatus 200 by inserting extension 210 downwardly so that groove 211 slips onto pivot peg 212 to secure the arm to the apparatus. Once fit into place contact region 208 pushes against flexible line 207 at contact surface 213 to pinch the line and prevent the flow of the gas/abrasive mixture. With lever 209 in place, the user of the apparatus uses his or her finger to press down on contact area to move contact 208 off the line 207 and allow the gas/abrasive mixture to flow to nozzle 206. Internal extension 215 aids in the positioning and operation of the device. Line 207 is shown having collars 216 and 217 that allow for easy removal and positioning of the line 207.

In an alternative embodiment, the apparatus of the invention is provided with a bypass gas line. For example, in the embodiment of FIG. 7, such as bypass gas line would connect line 204 and line 205. This bypass gas line would contain a valve such as a needle valve, and adjustment of the valve would serve to control the richness or leanness of the gas/abrasive mixture.

Figure 8:
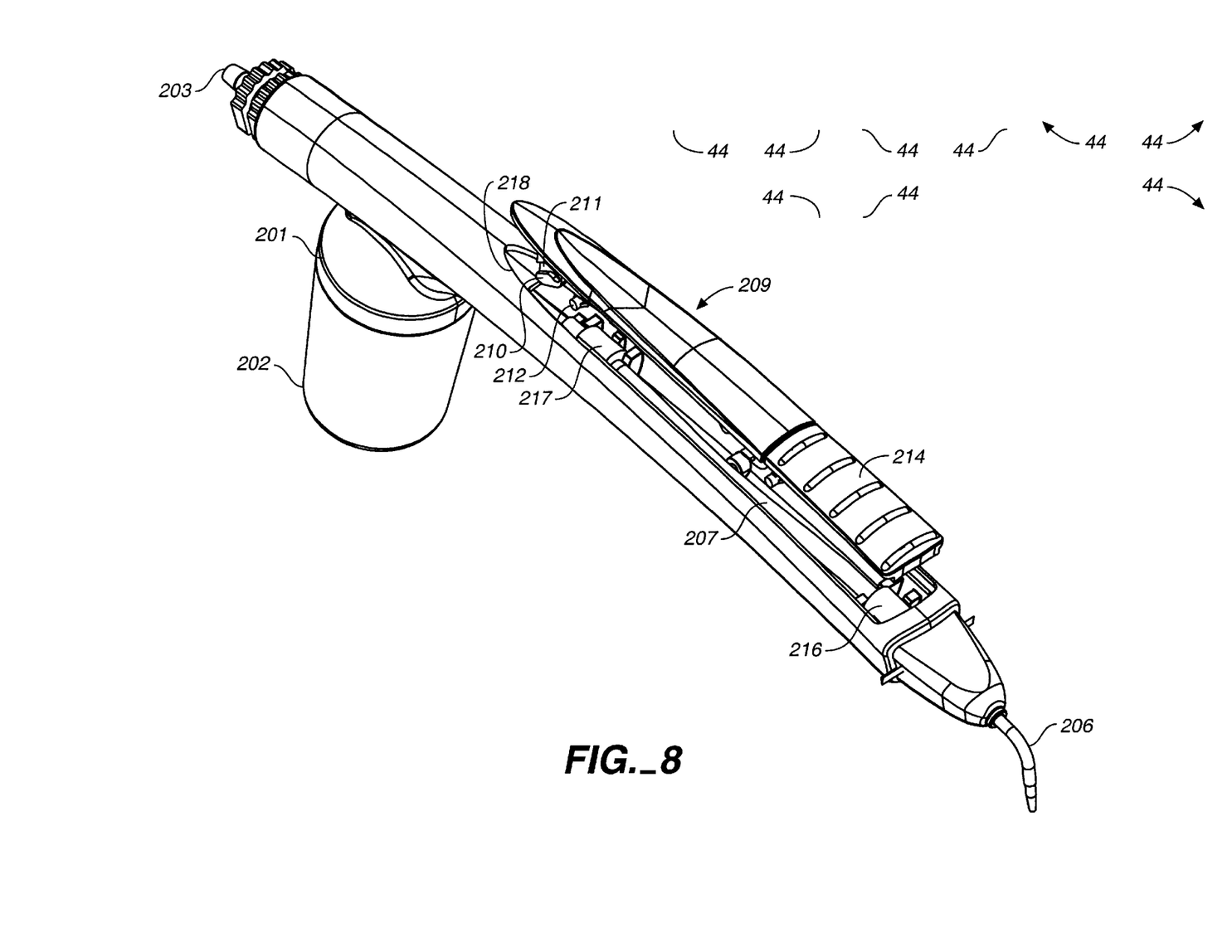
FIG. 8 is a partially exploded, top perspective view of the apparatus of this invention.

FIG. 8 shows a partially exploded, top perspective view of the apparatus 200 of FIG. 7, where similar numbers depict similar parts as in FIG. 7. Here one can see how lever 209 fits into opening 218 on the top of apparatus 200.

Figure 9:
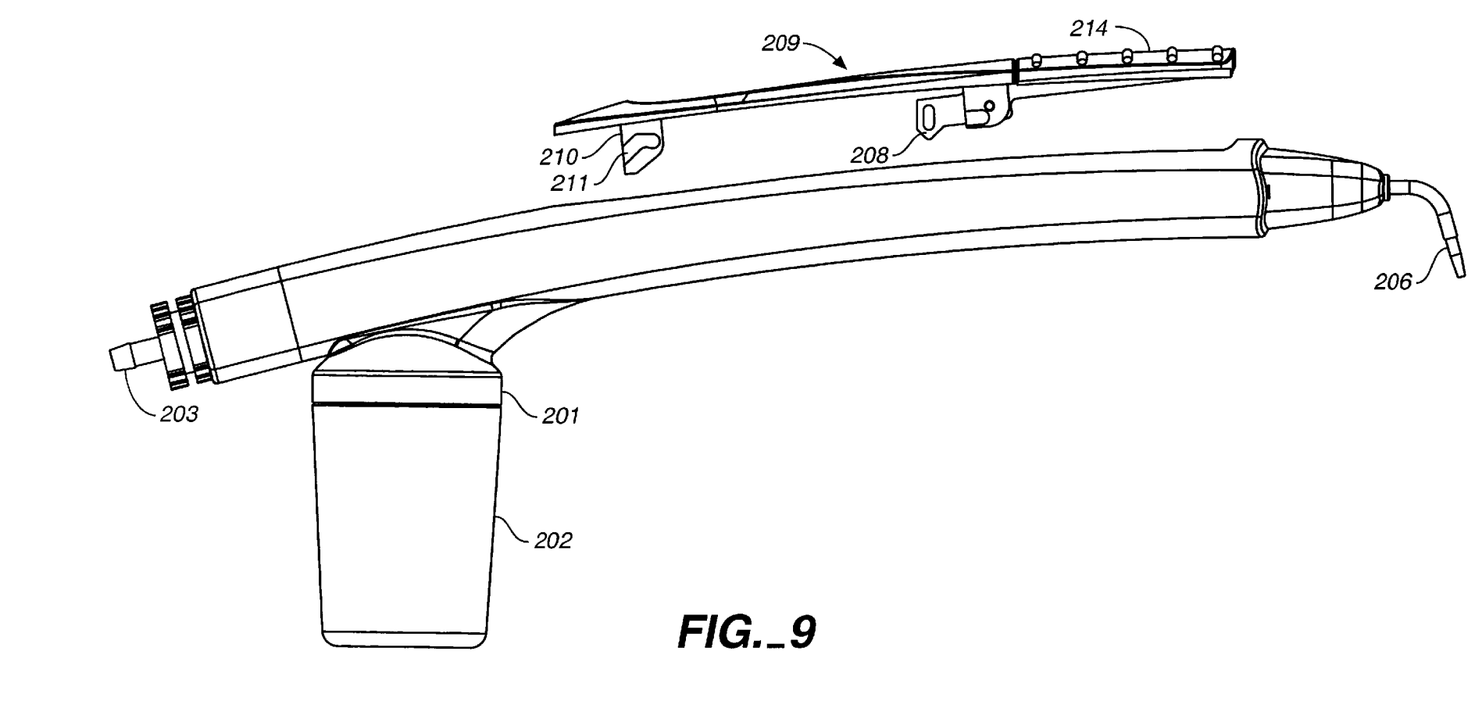
FIG. 9 is a side external view of the apparatus of the invention.

FIG. 9 is a side external view of apparatus 200, with the same numerals indicating the same parts.

Figure 10:
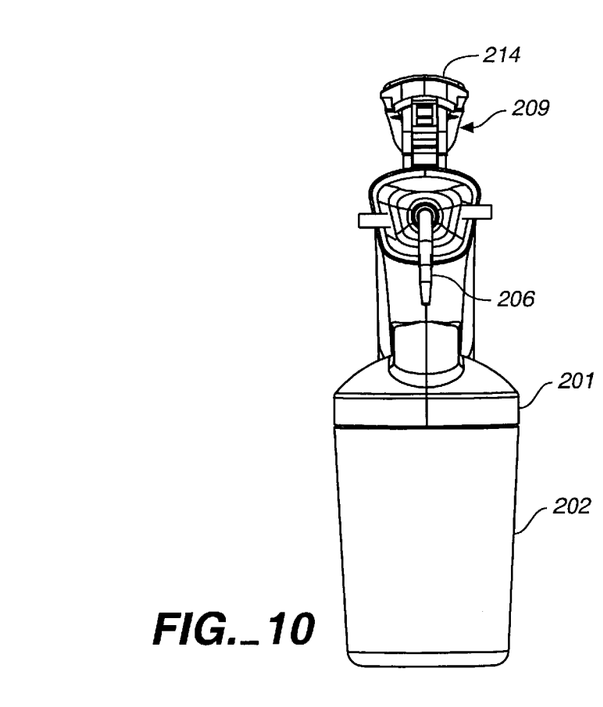
FIG. 10 is a front perspective view of the apparatus of this invention.

FIG. 10 is a front perspective view of apparatus 200, where the same numbers designate the same parts as in FIGS. 7–9.

Figure 11:
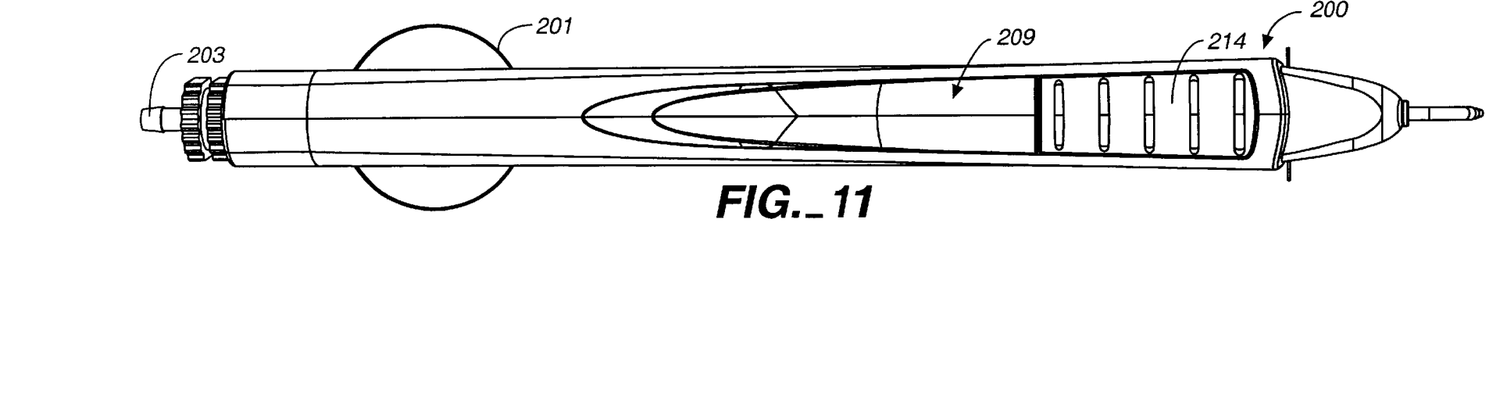
FIG. 11 is a top perspective view of the apparatus of this invention.

FIG. 11 is a top perspective view of the apparatus of FIGS. 7–10, where the same numbers designate the same parts.

Figure 12:
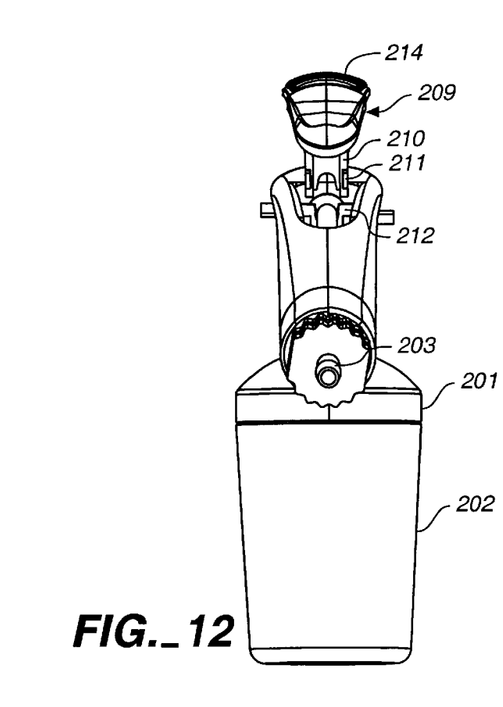
FIG. 12 is a rear perspective view of the apparatus of this invention.

FIG. 12 is a rear perspective view of the apparatus of FIGS. 7–11 where the same numbers designate the same parts.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A process for abrading a surface by delivering a stream of a mixture of a pressurized gas and a powdered abrasive material to the surface, which process comprises
    (A) connecting a source of pressurized gas to a hand-holdable apparatus that comprises
        (a) a container-receiving member detachably attached to a container containing a powdered abrasive material;
        (b) a discharge nozzle for directing the stream of the mixture of the gas/abrasive material against the surface;
        (c) a first flexible conduit having one end in fluid communication with the discharge nozzle and the other end in fluid communication with the attached container through the container-receiving member, wherein the flexible conduit is removable, is releasably connected at each end of the conduit, and each end of the first flexible conduit has a collar that is snugly, releasably retained to align one end of the flexible conduit with the discharge nozzle and the other end of the flexible conduit with a line communicating with the container for the powdered abrasive material attached to the container-receiving member;
        (d) a second optionally flexible conduit for connecting one end to an external gas source and the other end to the container-receiving member for the abrasive material container;
        (e) a manually-operated pinch valve located between the discharge nozzle and the container-receiving member for pinching the first flexible conduit to regulate the flow of the mixture of the gas/abrasive material to the discharge nozzle; and
        (f) a housing for parts (a)–(e),
    (B) directing the discharge nozzle against a surface to be abraded, and
    (C) actuating the pinch valve to allow a stream of pressurized gas/abrasive material to impinge upon the surface for a time sufficient to abrade the surface.

2. A process for abrading a surface by delivering a stream of a mixture of a pressurized gas and a powdered abrasive material to the surface, which process comprises
    (A) connecting a source of pressurized gas to a hand-holdable apparatus that comprises
        (a) a container-receiving member detachably attached to a container containing a powdered abrasive material;
        (b) a discharge nozzle for directing the stream of the mixture of the gas/abrasive material against the surface;
        (c) a first optionally flexible conduit having one end in fluid communication with the discharge nozzle and the other end in fluid communication with the attached container through the container-receiving member;
        (d) a second flexible conduit for connecting one end to an external gas source and the other end to the container-receiving member for the abrasive material container;
        (e) a manually-operated pinch valve for pinching the second flexible conduit to regulate the flow of the mixture of the gas/abrasive material to the discharge nozzle; and
        (f) a housing for parts (a)–(e),
    (B) directing the discharge nozzle against a surface to be abraded, and
    (C) actuating the pinch valve to allow a stream of pressurized gas/abrasive material to impinge upon the surface for a time sufficient to abrade the surface.

3. The process of claim 2, wherein the second flexible conduit is removable.

4. The process of claim 3, wherein the second flexible conduit is releasably connected at each end of the conduit.

5. The process of claim 4, wherein each end of the second flexible conduit has a collar that is snugly, releasably retained to align one end of the flexible conduit to the external gas source and the other end to the container-receiving member.

6. A process for abrading a surface by delivering a stream of a mixture of a pressurized gas and a powdered abrasive material, which process comprises
    (A) connecting a source of pressurized gas to a hand-holdable apparatus that comprises
        (a) an abrasive material pick-up assembly comprising (i) a container-receiving member for detachably receiving a container for the powdered abrasive material, (ii) two conduits, an inner conduit defined by a surrounding wall having a distal end away from the container-receiving member and proximal connected to the container-receiving member and an outer conduit defined by an outer wall, having analogous distal and proximal ends, wherein an intermediate passage is defined by the inner conduit wall and the outer-conduit wall, (iii) a container for holding the powdered abrasive material, the container having an open end and a closed end, which container is detachably connected to the container-receiving member through its open end and encloses the two conduits such that distal ends of the conduits are near the closed end of the container, (iv) a passageway through the wall of the inner conduit near its distal end, and (v) an optional passageway through the wall of the outer conduit near its distal end;
        (b) a discharge nozzle for directing a stream of a pressurized gas/abrasive mixture from the container against a surface to abrade the surface;
        (c) a pressurized gas delivery entry line for delivering a pressurized gas to the interior of the container through one of the conduits;
        (d) an exit line communicating with the interior of the container and leading to the discharge nozzle;
        (e) a pressure-actuated member that interrupts the flow of the gas/abrasive mixture from the container to the discharge nozzle, wherein when a pressurized gas is directed through the entry line into the inner conduit or intermediate passage, a pressure differential is created to force the powdered abrasive material from the container out the exit line and to the nozzle;
    (B) directing a stream of gas/abrasive material from the discharge nozzle against a surface to be abraded, and
    (C) allowing the pressurized gas to flow into the container to force the pressurized gas/abrasive material to impinge upon the surface for a time sufficient to abrade the surface.

7. The process of claim 6, wherein the exit line leading to the discharge nozzle is flexible, the pressure-actuated member is a pinch valve located between the discharge nozzle and the container-receiving member to constrict the flexible exit line to regulate the flow of the gas/abrasive mixture.

8. The process of claim 7, wherein the flexible exit line is removable.

9. The process of claim 8, wherein the flexible exit line is releasably connected at each end of the line.

10. The process of claim 9, wherein each end of the flexible exit line has a collar that is snugly, releasably retained to align one end of the line with the discharge nozzle and the other end of the line with a line communicating with the container for the powdered abrasive material attached to the container-receiving member.

11. The process of claim 6, wherein the gas delivery entry line is flexible and the pressure-actuated member is a pinch valve located to constrict the gas delivery flexible line to regulate the flow of the gas/abrasive mixture.

12. The process of claim 11, wherein the gas delivery flexible line is removable.

13. The process of claim 12, wherein the gas delivery flexible line is releasably connected at each end of the line.

14. The process of claim 13, wherein each end of the gas delivery flexible line has a collar that is snugly, releasably retained to align one end of the flexible line to the external gas source and the other end to the container-receiving member.

15. The process of claim 6, wherein the conduits of the abrasive material pick-up assembly are positioned to be concentric relative to each other.

16. The process of claim 15, wherein the outer conduit of the abrasive material pick-up assembly has its distal end positioned so that a gap of about 0.035 inch to about 0.125 inch exists between the distal end of the outer conduit and the closed end of the abrasive material container.

17. The process of claim 16, wherein the gap is about 0.095 inch.

18. The process of claim 15, wherein the passageway through the distal end wall of the inner conduit of the abrasive material pick-up assembly has a diameter of about 0.015 inch to about 0.030 inch.

19. The process of claim 18, wherein the diameter of the passageway is about 0.022 inch.

20. The process of claim 15, wherein there are two passageways through the distal end wall of the inner conduit of the abrasive material pick-up assembly, wherein each passageway has a diameter of about 0.015 inch to about 0.030 inch and is located 180° from the other.

21. The process of claim 15, wherein the inner conduit of the abrasive material pick-up assembly has a passageway through the wall of the inner conduit near its proximal end.

22. The process of claim 21, wherein the passageway near the proximal end of the inner conduit has a diameter of about 0.025 inch to about 0.035 inch.

23. The process of claim 22, wherein the passageway near the proximal end of the inner conduit is 0.031 inch.

24. The process of claim 15, wherein pressurized gas is directed into the inner conduit and the gas/abrasive material mixture is directed out of the container through the intermediate passageway formed between the outer wall of the inner conduit and the inner wall of the outer conduit and to the discharge nozzle.

25. The process of claim 15, wherein pressurized gas is directed into the intermediate passage formed between the outer wall of the inner conduit and the inner wall of the outer conduit and the gas/abrasive material is directed out of the container through the inner conduit.

26. An apparatus for delivering a stream of a mixture of a gas and a powdered abrasive material to a surface, which apparatus comprises:
(a) a container-receiving member for detachably receiving a container for the powdered abrasive material;
(b) a discharge nozzle for directing the stream of the mixture of the gas/abrasive material against a surface;
(c) a first flexible conduit having one end in fluid communication with the discharge nozzle and the other end in fluid communication with the container, when attached, through the container-receiving member, wherein the first conduit is removable and is releasably connected at each end of the conduit, and each end of the first flexible conduit has a collar that is snugly, releasably retained to align one end of the flexible conduit with the discharge nozzle and the other end of the flexible conduit with a line communicating with the container for the powdered abrasive material attached to the container-receiving member;
(d) a second optionally flexible conduit for connecting one end to an external gas source and the other end to the containing-receiving member for the abrasive material container;
(e) a manually-operated pinch valve located between the discharge nozzle and the container-receiving member for pinching the first flexible conduit to regulate the flow of the mixture of the gas/abrasive material to the discharge nozzle; and
(f) a housing for parts (a)–(e).

27. The apparatus of claim 26, which further comprises a bypass gas line having a valve, said gas line connecting the first and second conduits.

28. An apparatus for delivering a stream of a mixture of a gas and a powdered abrasive material to a surface, which apparatus comprises:
(a) a container-receiving member for detachably receiving a container for the powdered abrasive material;
(b) a discharge nozzle for directing the stream of the mixture of the gas/abrasive material against a surface;
(c) a first optionally flexible conduit having one end in fluid communication with the discharge nozzle and the other end in fluid communication with the container, when attached, through the container-receiving member;
(d) a second flexible conduit for connecting one end to an external gas source and the other end to the container-receiving member for the abrasive material container;
(e) a manually-operated pinch valve for pinching the second flexible conduit to regulate the flow of the mixture of the gas/abrasive material to the discharge nozzle; and
(f) a housing for parts (a)–(e).

29. The apparatus of claim 28, wherein the second flexible conduit is removable.

30. The apparatus of claim 29, wherein the second flexible conduit is releasably connected at each end of the conduit.

31. The apparatus of claim 30, wherein each end of the second flexible conduit has a collar that is snugly, releasably retained to align one end of the flexible conduit to the external gas source and the other end to the container-receiving member.

32. A hand-holdable apparatus for delivering a stream of a gas and a powdered abrasive material to a surface, which apparatus comprises:
(a) an abrasive material pick-up assembly comprising (i) a container-receiving member for detachably receiving a container for the powdered abrasive material, (ii) two conduits, an inner conduit defined by a surrounding wall having a distal end away from the container-receiving member and proximal end connected to the container-receiving member and an outer conduit defined by an outer wall, having analogous distal and proximal ends, wherein an intermediate passage is defined by the inner conduit wall and the outer-conduit wall, (iii) a container for holding the powdered abrasive material, the container having an open end and a closed end, which container is detachably connected to the container-receiving member through its open end and encloses the two conduits such that distal ends of the conduits are near the closed end of the container, (iv) a passageway through the wall of the inner conduit near its distal end, and (v) an optional passageway through the wall of the outer conduit near its distal end;

(b) a discharge nozzle for directing a stream of a pressurized gas/abrasive mixture from the container against a surface to abrade the surface;

(c) a gas delivery entry line for delivering a pressurized gas to the interior of the container through one of the conduits;

(d) an exit line communicating with the interior of the container and leading to the discharge nozzle;

(e) a pressure-actuated member that interrupts the flow of the gas/abrasive mixture from the container to the discharge nozzle, wherein when a pressurized gas is directed through the entry line into the inner conduit or intermediate passage, a pressure differential is created to draw the powdered abrasive material from the container out the exit line and to the nozzle.

33. The apparatus of claim 32, wherein the exit line leading to the discharge nozzle is flexible, the pressure-actuated member is a pinch valve located between the discharge nozzle and the container-receiving member to constrict the flexible exit line to regulate the flow of the gas/abrasive mixture.

34. The apparatus of claim 33, wherein the flexible exit line is removable.

35. The apparatus of claim 34, wherein the flexible exit line is releasably connected at each end of the line.

36. The apparatus of claim 35, wherein each end of the flexible exit line has a collar that is snugly, releasably retained to align one end of the line with the discharge nozzle and the other end of the line with a line communicating with the container for the powdered abrasive material attached to the container-receiving member.

37. The apparatus of claim 32, wherein the gas delivery entry line is flexible and the pressure-actuated member is a pinch valve located to constrict the gas delivery flexible line to regulate the flow of the gas/abrasive mixture.

38. The apparatus of claim 37, wherein the gas delivery flexible line is removable.

39. The apparatus of claim 38, wherein the gas delivery flexible line is releasably connected at each end of the line.

40. The apparatus of claim 39, wherein each end of the gas delivery flexible line has a collar that is snugly, releasably retained to align one end of the flexible line to the external gas source and the other end to the container-receiving member.

41. The apparatus of claim 32, wherein the conduits of the abrasive material pick-up assembly are positioned to be concentric relative to each other.

42. The apparatus of claim 41, wherein the outer conduit of the abrasive material pick-up assembly has its distal end positioned so that a gap of about 0.035 inch to about 0.125 inch exists between the distal end of the outer conduit and the closed end of the abrasive material container.

43. The apparatus of claim 42, wherein the gap is about 0.095 inch.

44. The apparatus of claim 41, wherein the passageway through the distal end wall of the inner conduit of the abrasive material pick-up assembly has a diameter of about 0.015 inch to about 0.030 inch.

45. The apparatus of claim 44, wherein the diameter of the passageway is about 0.022 inch.

46. The apparatus of claim 41, wherein there are two passageways through the distal end wall of the inner conduit of the abrasive material pick-up assembly, wherein each passageway has a diameter of about 0.015 inch to about 0.030 inch and is located 180° from the other.

47. The apparatus of claim 41, wherein the inner conduit of the abrasive material pick-up assembly has a passageway through the wall of the inner conduit near its proximal end.

48. The apparatus of claim 47, wherein the passageway near the proximal end of the inner conduit has a diameter of about 0.025 inch to about 0.035 inch.

49. The apparatus of claim 48, wherein the passageway near the proximal end of the inner conduit is 0.031 inch.

50. The apparatus of claim 41, wherein pressurized gas is directed into the inner conduit and the gas/abrasive material mixture is directed out of the container through the annular passageway formed between the outer wall of the inner conduit and the inner wall of the outer conduit and to the discharge nozzle.

51. The apparatus of claim 41, wherein pressurized gas is directed into the annular passage formed between the outer wall of the inner conduit and the inner wall of the outer conduit and the gas/abrasive material is directed out of the container through the inner conduit.

* * * * *